United States Patent [19]

La Rocca

[11] Patent Number: 4,776,793
[45] Date of Patent: Oct. 11, 1988

[54] DENTAL ASPIRATOR

[76] Inventor: Nina La Rocca, 13873 Trenton Trail, Middleburgh Hts., Ohio 44130

[21] Appl. No.: 97,756

[22] Filed: Sep. 17, 1987

[51] Int. Cl.$^4$ ............................................. A61C 17/04
[52] U.S. Cl. ..................................................... 433/96
[58] Field of Search ............................ 433/91, 93, 96; 128/132 R, 136

[56] References Cited

U.S. PATENT DOCUMENTS 3,139,088  6/1964  Galleher ............................... 428/136
3,460,255  8/1969  Hutson ................................... 433/91

Primary Examiner—Robert Peshock
Attorney, Agent, or Firm—J. Helen Slough

[57] ABSTRACT

A dental appliance for attachment to an aspirator operated by power vacuum means wherein the tube projecting into the mouth of a patient to evacuate fluid and debris therefrom is provided with openings of preferably funnel shape disposed in spaced relation about the circumference of the tube and positioned adjacent to a generally cup shaped receptacle secured or integral with the tube to catch drippings therefrom of excess fluids or debris not caught by the tube portion projected into the mouth of the patient to prevent splashing therefrom.

5 Claims, 1 Drawing Sheet

DENTAL ASPIRATOR

This invention relates to dental aspirators which are suction devices used to withdraw fluids and debris from the mouth of a patient during the course of dental work on said patient and particularly relates to power driven aspirators.

In the past, dental tools have been provided with guards, receptacles and anti-splash devices of the type shown in U.S. Pat. No. 2,731,732, wherein the guard is placed in the mouth and protects the depressed lining of the mouth or the tongue from engagement with a rotating grinding wheel; U.S. Pat. No. 4,424,036, which provides an inverted anti-splash cup spaced from water delivery means which is placed in the mouth of the patient, and which is transparent so that the dental prophylaxis treatment may be observed; U.S. Pat. No. 3,090,172, where the dental tool is an aspirator but the receptacle is also positioned in the patient's mouth; and U.S. Pat. No. 4,611,992 wherein the anti-splash means is placed over a tooth being treated for collection of debris and liquid from the mouth of the patient.

The present invention provides an anti-splash device to provide a tip for a dental aspirator which is a suction device used to draw fluid and debris which accumulates due to the use of high powered tools, water sprays, cutting instruments, etc., from the mouth of the dental patient. The aspirator has a tub which projects into the mouth of the patient being treated. The aspirator is used to evacuate a patient's mouth during dental procedures of fluid and debris, for example saliva, blood, water and other debris and avoid splashing of the same. In the device of my invention, the tube is provided with preferably a plurality of apertures about the circumference of a portion of the tube disposed exteriorly of the mouth of the patient adjacent and immediately below an umbrella or cup shaped transparent shield or skirt carried by the tube. The tube wall portions surrounding the apertures are inclined upwardly and outwardly of the remaining tube portions and the inclination of the same increases in portions closest to the rim of the shield or skirt wherefor said apertures communicate with the under surfaces of the shield to which excess spray of fluid or debris is directed from the mouth of the patient and is redirected by dripping from the covering shield into the widened mouth of the apertures or openings in the tube to be drawn off by the suction effect of the aspirator. During most dental procedures a water and air syringe is constantly in use, causing splashing of fluids and debris from the mouth. The power vacuum system employed to withdraw fluid by an aspirator causes the liquids and debris to be evacuated through the tube.

Figure 1:
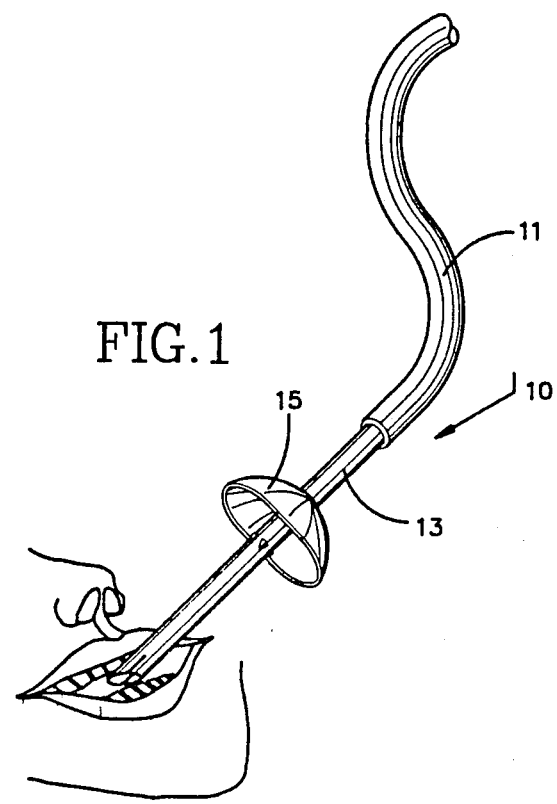
FIG. 1 is a perspective view of the open mouth of a patient with the device of my invention shown in place.
Figure 2:
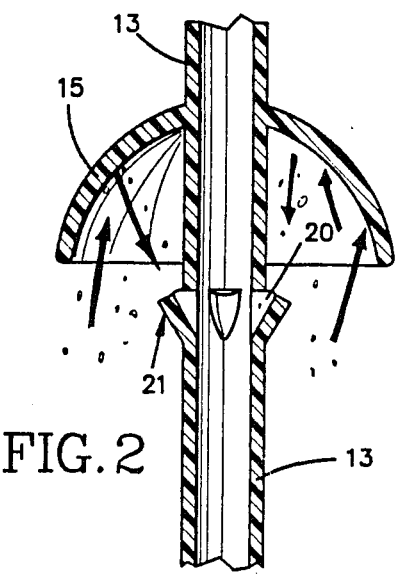
FIG. 2 is an enlarged sectional view of a portion of the improved aspirator of my invention showing the apertured and skirt portions of this invention.
Figures 3, 4:
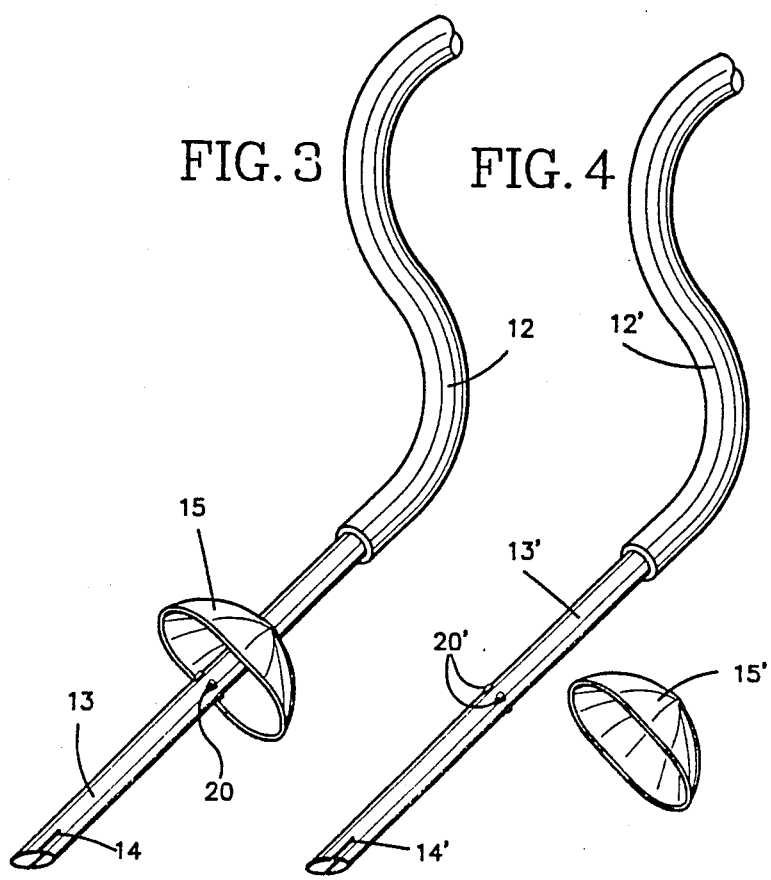
FIG. 3 is a perspective view of an integrally formed aspirator of the invention.
FIG. 4 is a perspective view similar to that of FIG. 3 wherein the skirt is removed from the aspirator tube, said skirt being adapted to be detachably secured to the aspirator tube as shown in FIG. 3.

Referring now to the drawings in which like parts are designated by like reference characters, in FIGS. 1 to 3 inclusive is shown a power driven dental tool known as a aspirator 10, which aspirator is used to draw fluids and debris from the mouth of a patient. The aspirator 10 comprises an elongated flexible hollow tube 11 having a relatively more rigid tip portion 13 which, in the form shown, is provided with slots 14 adjacent an end thereof, which tip extends into the mouth of the patient. The outer end of the tube of the aspirator is connected to a hose 12 of a conventional aspirator or other vacuum source (not shown), drawing by suction, liquid and debris from the mouth of the patient. The said liquid and debris etc., accumulate therein due to the use of high powered tools, water sprays, cutting instruments, etc., by the dentist or dental assistant during treatment. A preferably cup shaped receptacle, shield or open cylinder 15 is secured to a portion of the tip end of the aspirator and, as shown in FIG. 2, may be integral with the same or detachably secured thereto, as indicated in FIG. 4 at 15'.

The receptacle 15, 15' is symmetrically disposed about the axis of the tube in open inverted position and the outer periphery thereof is disposed adjacent and immediately above openings 20 provided in spaced relation about the circumference of the tube tip. The openings 20 are, as illustrated herein, provided in the tube walls, which walls are distended about said openings, as best shown in FIG. 2 at 21, to provide greater enlargement in those portions of the openings adjacent the outer rim of the receptacle 12, as a result excess fluid and debris caught by the receptacle is redirected into the tube through said openings and hence suctioned off by the aspirator. The openings are, as shown, preferably of funnel shape. The receptacle may be of any material such as paper, celluloid, or the like and should preferably be transparent to enable the dentist or his assistant to observe the same.

Figure 5:
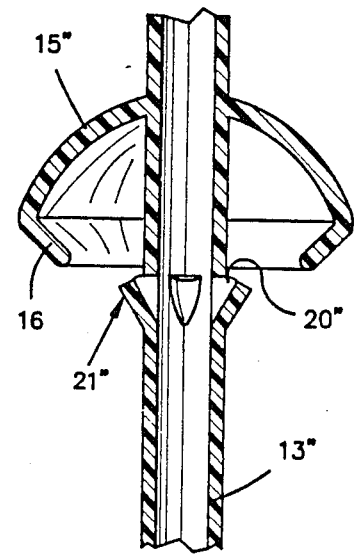
FIG. 5 is an enlarged sectional view of the modification of the aspirator of my invention.

The receptacle may be of varied form as for example as shown in FIG. 5 provided with inturned peripheral sides but should be essentially of dome shape having a curved upper open umbrella or cup form and adapted to be disposed in such position on the tube with respect to the openings as to enable excess fluid or debris to drop therefrom into the openings or vents in the tubular means.

While I have described my invention in connection with preferred embodiments, it is to be understood that departures may be made therefrom without however departing from the spirit of my invention and the appended claims.

What I claim is:

1. A dental appliance for collecting and removing liquid and debris from the mouth of a patient during the conduct of dental operations therein comprising: tubular suction means adapted to be inserted into the mouth of the patient, power vacuum means adapted to withdraw said liquid and debris from the mouth through said tubular means, said tubular means being provided with a funnel shaped opening in a portion of the tubular means spaced outwardly of the mouth, an inverted cup shaped receptacle disposed on said tubular means above said opening adapted to receive excess fluid and debris from the mouth and to deposit the same into the opening and into the appliance, tubular suction means to withdraw the same.

2. A dental appliance according to claim 1 wherein a plurality of openings are provided in the tubular means in spaced relation about the circumference of the tube.

3. A dental appliance according to claim 1 wherein walls of the tubular means in which the opening is provided is distended to provide a relatively wide mouth for the reception of drippings from the receptacle.

4. A dental appliance according to claim 1 wherein the receptacle is integral with the tube.

5. A dental appliance according to claim 1 wherein the receptacle is provided with inwardly turned peripheral sides.

* * * * *

UNITED STATES PATENT AND TRADEMARK OFFICE
CERTIFICATE OF CORRECTION

PATENT NO. : 4,776,793
DATED : October 11, 1988
INVENTOR(S) : Nine La Rocca

It is certified that error appears in the above-identified patent and that said Letters Patent is hereby corrected as shown below:

In Column 1, Line 29, the word "tub" should be "tube".

Signed and Sealed this

Twenty-eighth Day of March, 1989

Attest:

DONALD J. QUIGG

Attesting Officer

Commissioner of Patents and Trademarks